United States Patent [19]

Hunt et al.

[11] Patent Number: 4,590,928
[45] Date of Patent: May 27, 1986

[54] SURGICAL IMPLANT

[75] Inventors: Michael S. Hunt, Edenvale; Peter J. Mundell, Verwoerdburg; Angus E. Strover, Halfway House, all of South Africa

[73] Assignee: South African Invention Development Corporation, Pretoria, South Africa

[21] Appl. No.: 304,508
[22] Filed: Sep. 22, 1981

[30] Foreign Application Priority Data

Sep. 25, 1980 [ZA] South Africa .................. 80/5957

[51] Int. Cl.⁴ .............................................. A61F 1/00
[52] U.S. Cl. ................................. 128/92 D; 128/92 B; 128/92 C; 623/13; 623/16
[58] Field of Search ............ 128/92 C, 92 BB, 92 BC, 128/92 D, 92 G, 92 B; 3/1, 1.9, 1.81, 1.811, 1.812, 1.813

[56] References Cited

U.S. PATENT DOCUMENTS

| | | | |
|---|---|---|---|
| 2,301,244 | 11/1942 | Bishop | 411/57 |
| 3,233,800 | 2/1966 | Catania | 128/337 |
| 3,513,484 | 5/1970 | Hausner | 3/1 |
| 3,623,164 | 11/1971 | Bokros | 3/1.9 |
| 3,707,006 | 12/1972 | Bokros | 128/92 CA |
| 3,896,500 | 7/1975 | Rambert et al. | 3/1 |
| 4,013,071 | 3/1977 | Rosenberg | 3/1.9 |
| 4,127,902 | 12/1978 | Homsy | 3/1.9 |
| 4,149,277 | 4/1979 | Bokros | 3/1 B |
| 4,182,341 | 1/1980 | Perri | 128/339 |
| 4,329,743 | 5/1982 | Alexander et al. | 3/1.9 |

FOREIGN PATENT DOCUMENTS

| | | |
|---|---|---|
| 0012146 | 11/1978 | European Pat. Off. . |
| 0013862 | 1/1979 | European Pat. Off. . |
| 0008620 | 6/1979 | European Pat. Off. . |
| 0030583 | 12/1979 | European Pat. Off. . |
| 2138735 | 5/1972 | France . |
| 2254298 | 8/1975 | France .................. 128/92 B |
| 2350825 | 4/1977 | France . |
| 2361093 | 8/1977 | France . |
| 1390445 | 4/1975 | United Kingdom . |
| 1513235 | 6/1978 | United Kingdom . |
| 1580691 | 12/1980 | United Kingdom . |
| 2059777 | 4/1981 | United Kingdom . |
| 2058575 | 4/1981 | United Kingdom . |
| 1602834 | 11/1981 | United Kingdom .................. 128/92 |
| 271713 | 9/1970 | U.S.S.R. .................. 128/92 B |
| 0584855 | 12/1977 | U.S.S.R. .................. 128/92 B |

OTHER PUBLICATIONS

"Internal Fracture Fixation with Partially Degradable Plates" Alexander et al. (In Press, Proceedings Northeast Bioengineering Conference, 1981).
"Medical Collateral Ligament Replacement with a Partially Absorbable Tissue Scaffold"-Parsons et al. (In Press, Proceedings of the Northeast Bioengineering Conference, 1981).
"Soft Tissue Attachment of Filamentious Carbon-Absorbable Polymer Tendon and Ligament Replacement Aragona et al. (In Press, Clinical Orthopaedics and Related Research).
"Avdel Drive Rivet" brochure, by Avdel Ltd. Leaflet L21 Issue 2 4/76.
"The Development of a Variable Stiffness, Absorbable Composite", by S. F. Corcoran et al. published in Current Concepts of Internal Fixation of Fractures, pp. 36–45, Edited by H. K. Uhthoff et al. (Springer-Verlag, Berlin–Heidelberg, 1980).
"The Role of Bioengineering in Orthopedics" by A. B. Weiss et al., 7 Primary Care, pp. 317–329 (No. 2, Jun. 1980).
"Canine Patellar Tendon Replacement with a Polylactic Acid Polymer-Filamentous Carbon Tissue Scaffold" Alexander et al. (Accepted for publication in Orthopedic Review).

Primary Examiner—Richard J. Apley
Assistant Examiner—David J. Isabella
Attorney, Agent, or Firm—Ladas & Parry

[57] ABSTRACT

The invention provides a surgical implant in the form of a stud for anchoring in a hole formed in bone. The stud has an elongated cylindrical body which is tubular and which has a head at one end and a passage along its interior. A pin is insertable into the passage from the end having the head to expand the body transversely to anchor it in the hole. The body and pin are of biocompatible material and the body contains carbon fibres embedded in and extending longitudinally along its interior.

The invention provides also a surgical implant kit including the stud, and a method of surgery employing the stud and kit.

13 Claims, 17 Drawing Figures

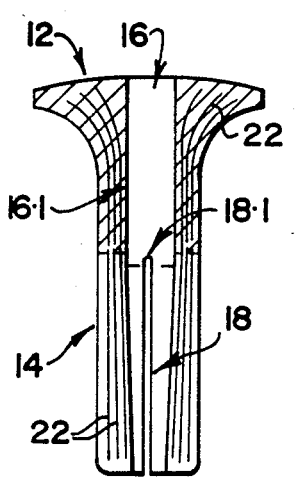
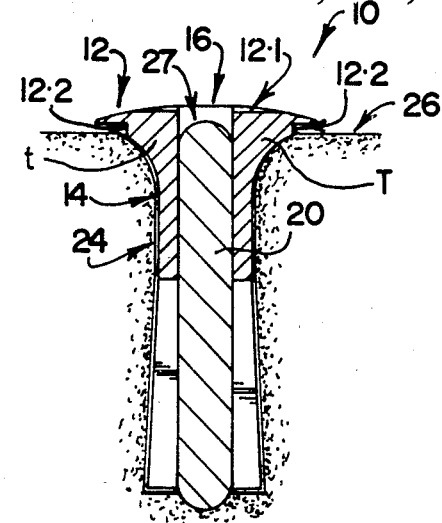
FIG. 7  FIG. 8
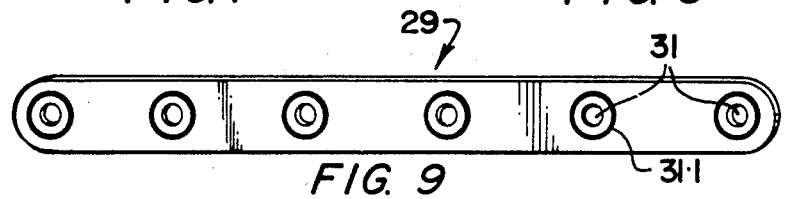
FIG. 9
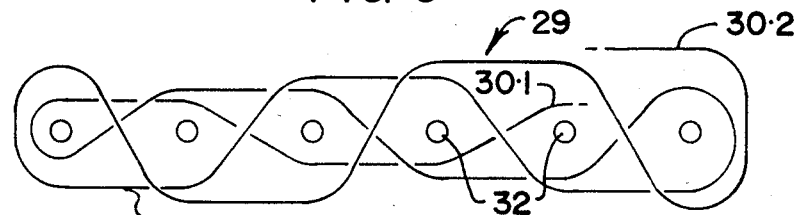
FIG. 10
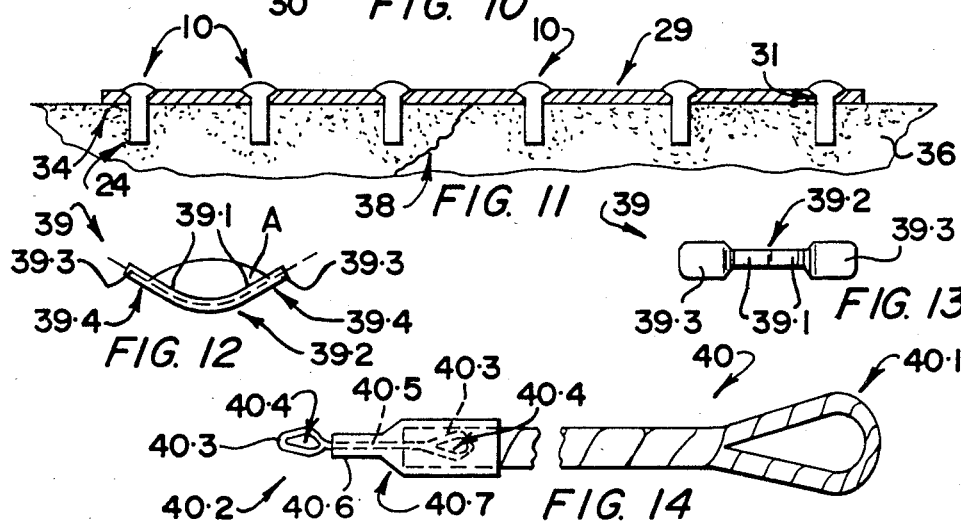
FIG. 11
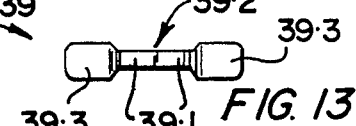
FIG. 12  FIG. 13
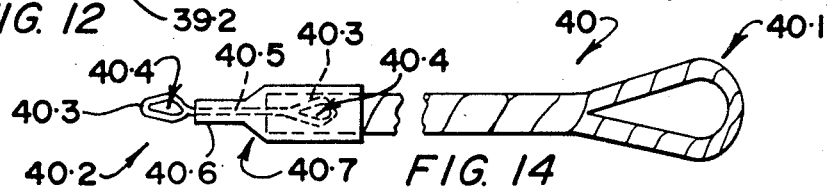
FIG. 14

SURGICAL IMPLANT

This invention relates, broadly, to surgical implants. More particularly, it relates to a surgical implant, to surgical implant kits comprising said implant, and to the use thereof in surgery.

According to the invention there is provided a surgical implant in the form of a stud for anchoring in a hole formed in a bone, the stud having an elongated cylindrical body which is tubular and has a head at one end thereof and a passage along its interior opening out at opposite ends thereof, the stud including a pin insertable into the passage from the end having the head to expand the body transversely, the body and pin being of a biocompatible material or materials, and the body containing carbon fibres embedded therein, and extending longitudinally relative to the body.

The inner surface of the body defining the passage should be smooth in the longitudinal direction and the pin should have a radially outwardly facing outer surface which is also smooth in the longitudinal direction, so that the pin is axially slidable into the passage. Similarly, the radially outwardly facing outer cylindrical surface of the body should be of substantially constant diameter and should be smooth in both the longitudinal and circumferential directions.

The expression "smooth in the longitudinal direction" with regard to said inner surface of the body defining the passage, said outer surface of the pin and the outer cylindrical surface of the body, means that said surfaces have no circumferentially extending depressions or projections; and, similarly "smooth in the circumferential direction" with regard to the cylindrical outer surface of the body of the stud means that it has no longitudinally extending depressions or projections.

By "biocompatible" is meant that the material can be left in a human or animal body for an extended or an indefinite period without causing any adverse physiological action, and the term includes substances such as gelatine, e.g. cross-linked gelatine, which can eventually be absorbed and excreted by the body, and can be occupied or replaced by invasive bodily tissue, and are in this sense biodegradable.

The body of the stud may have one or more circumferentially spaced slits in its wall, extending away from its end remote from the head to facilitate expansion thereof by the pin. The pin may be cylindrical, at least part of the passage tapering in a direction towards its end remote from the head, whereby the body is transversely expandible by insertion of the pin from the direction of the head along the passage into said tapered part.

The pin may be shorter than the passage, so that it can be inserted into the body with its one end at the end of the passage remote from the head, and its other end inwardly recessed from the end of the passage at the head. This recess can form a drill guide for the end of a drill if the stud is ever to be removed by drilling.

The head may be shaped for engagement with a tool for turning the body about its axis, e.g. by having a slot for a screw driver, or one or more flats for a socket spanner. The head may be eccentric or offset transversely to one side with regard to the body, for tensioning a tow looped around it.

Apart from cross-linked gelatine, other biocompatible matrix materials, for forming the matrix within which the carbon fibres of the stud (and other implants described hereunder) are embedded, include polysulphones, epoxy resins or carbon itself, and will be selected to have the desired biochemical and mechanical characteristics required for the intended use of the implant. In general the material in the body should be able to remain in place with no undesirable effects on itself or the surrounding tissue. When the matrix is carbon itself, the implant can be made by carbonizing the carbon fibres in a carbon containing precursor matrix, such as pitch or a phenolic resin, or gas phase deposition of carbon on the fibres from a heated hydrocarbon gas.

For the stud and other elongated implants described herein the carbon fibres may extend over substantially the whole length of the implant and may be continuous and unbroken along the whole of said length. However they need not be parallel with the length of the implant over its whole length and it is contemplated that shorter staple fibres, overlapping or staggered along the length of the implant will also have utility. For convenience in making the implants, the matrix material may be flexible and thermoplastic.

The carbon fibres in the stud or like implant will provide it with substantial tensile and bending strength, but the shear strength in the longitudinal direction, of the implant (when stress tends to slide the fibres longitudinally over one another) will depend on the matrix material and the lengths of the fibres which are in side-by-side contact with one another. For this reason it is preferred not to machine the implants but to form them with the fibres being curved if necessary but whole (unbroken) as far as possible, to resist any tendency for the implant to fail by shearing when it is stressed, the fibres instead being placed in tension.

Thus to make the stud or like implant, the fibres may be placed or arranged to occupy positions and to extend in directions where their mechanical properties will eventually be most useful, before the matrix is formed. Instead, the implant may be post formed, from a suitable blank of more or less uniform cross-section, the matrix being thermoplastic and being heated to permit formation of the implant by plastic deformation thereof. Thus, axial compression of a tubular blank for a stud may be used to thicken one end thereof to form a head, forcing the fibres to curve outwardly so that when the head is in use pulled in the axial direction, the fibres in the head are load carrying and stressed, thereby reducing any tendency for the head to fail by shearing of the matrix, as would be the case if the stud was turned down from a blank of enlarged cross-section and having straight, parallel fibres. According to this method of making a stud, the central passage can be formed simultaneously, by inserting a tapered pin down the interior of the blank while it is heated. The slits may be cut as a final step, and as the cuts will be parallel to the fibres of the shank, they will cause little loss in tensile strength. Instead the blank may be solid, with a tapered pin being used to form the central passage.

The invention extends to a surgical implant kit which comprises:

a flexible cord for connecting together two bones in an animal or human body;

a stud as described above for insertion into a hole formed in bone, for anchoring said cord; and an anchor member for location at the mouth of a passage formed in bone from which the cord emerges, for anchoring the cord at a position spaced from the stud to prevent withdrawal of the cord along the passage when the cord extends along the passage under tension between the anchor member and stud, the cord and anchor member being of a biacompatible material or materials.

The cord may comprise a tow or skein of carbon fibres impregnated with a biocompatible material which causes the fibres to adhere to one another and which reduces the surface area of the tow. The biocompatible material which impregnates the tow may comprise gelatine which has been sterilized by irradiation and which contains a bactericide, and the carbon fibres may be arranged in the form of a braided or twisted rope, having, at one end thereof, and a loop for engagement with the anchor member.

The anchor member may be in the form of a toggle shaped anchor bar having two limbs which extend away from each other from a corner where they make an obtuse angle with each other, the anchor bar having a radius of curvature which exceeds the diameter of the carbon fibres of the tow by a factor of more than about $10^2$, and the free ends of the limbs of the anchor bar being flattened to provide bearing surfaces for bearing against bone at the mouth of a passage through bone.

Instead, one end of the cord may be permanently connected to the anchor member for preventing withdrawal of the cord along a passage formed in bone.

The cord may be provided with a connector at one end thereof for connection to a fish wire or the like for pulling the cord through a passage formed in bone or like tissue. The connector may comprises a length of malleable wire having a loop defining an eye at each end thereof, one of the loops of the wire being embedded in the end of the cord and adhesively secured thereto, the material of the cord being adhesively secured to itself through the eye of said embedded loop and the part of the cord containing adhesive, and the wire between the end of the cord and the loop at the free end of the wire, being covered by a sleeve in the form of a heat shrunk length of plastics tubing which tapers from where it surrounds the cord to where it surrounds the wire.

The invention extends to an anchor member for use as part of a kit as described above, which is in the form of a toggle shaped anchor bar having two limbs which extend away from each other from a corner where they make an obtuse angle with each other, the anchor bar comprising a biocompatible material containing carbon fibres extending lengthwise along it and having the free ends of its limbs flattened to provide bearing surfaces for bearing against bone at the mouth of a passage through bone.

The invention extends also to a surgical implant kit which comprises an elongated bone plate formed from a biocompatible material or materials and having a plurality of holes therethrough, and a plurality of studs as described above, for passing respectively through the holes in the bone plate and into holes formed in bone, for anchoring the bone plate to bone.

The bone plate may be elongated, comprising biocompatible material within which is embedded a plurality of carbon fibres extending at least partially lengthwise along the bone plate.

The invention extends still further to a bone plate for use as part of a kit as described above, which comprises biocompatible material within which is embedded a plurality of carbon fibres extending at least partially along the length of the bone plate, the bone plate having a plurality of holes therethrough for receiving studs.

The bone plate may be elongated, having parallel longitudinal side edges, the holes being arranged to extend in a spaced series along the bone plate, substantially midway between the longitudinal side edges of the plate.

The invention thus permits connecting two bones or bone portions together in animal or human surgery, by:
forming at least one hole in at least one of the bones or portions;
anchoring a stud as described above in said hole;
connecting a connecting member to said stud; and
connecting the connecting member to the other bone or portion.

A hole may be formed in one bone, a passage being formed in the other bone, a connecting member in the form of a flexible cord being pulled through the passage so that it extends through the passage from an anchor member located at one end of the passage and then to the hole, the cord being pulled towards the hole and away from the anchor member to draw the anchor member up against the bone at the mouth of the passage and to tension the cord, and the cord being connected to the stud to maintain said tension.

The cord may have a connector at one end thereof, pulling the cord through the passage being by means of a fish wire or the like connected to the connector and the end of the cord having the connector being connected to the stud.

The cord may have a loop at one end thereof, the method including connecting the cord to the anchor member by threading the anchor member through the loop after the cord has been pulled through the passage and prior to tensioning the cord.

The method may include, after the cord has been pulled through the passage, and prior to connecting it to the stud, removing the part of the cord provided with the connector.

Connecting the cord to the stud may comprise looping the cord around the stud in the fashion of a rope around a bollard, and suturing the cord to the bone in which the stud is anchored, or to tissue connected to said bone, to keep the cord under tension.

The method may include, after the cord has been looped around the stud and before the stud has been permanently anchored in the hole, driving the stud into the hole to grip the cord between the head of the stud and the bone at the mouth of the hole.

The method may include after the cord has been looped around the stud and before the stud has been permanently anchored in position, turning the stud about its axis by means of a tool engaging the head of the stud, to tension the cord.

The method may include forming a passage in each of the bones, the cord being pulled through both passages so that it extends from the anchor member, through the passage at whose end the anchor member is located, and then through the other passage to the hole for the stud.

The bones may be bones of the human leg at a knee joint wherein a cruciate ligament has been damaged, the passages opening out into the knee joint at or adjacent the roots of the damaged ligament, so that the cord extends from one passage to the other along the path normally occupied by the damaged ligament, the method including suturing the damaged ligament so that it extends under tension along the cord from the one bone to the other. When the ligament has been damaged by becoming detached from one of the bones, the method may include forming the hole in the bone from which the ligament has become detached, threading the cord along the interior of the ligament and pulling the detached end of the ligament to said bone containing the hole by a suture attached to said detached end of the ligament, the suture being anchored to the stud to extend under tension alongside the cord.

Instead, a hole may be formed in each of two bones, the connecting member being in the form of a flexible cord and the method comprising attaching the cord under tension to studs anchored respectively in the holes.

Anchoring the cord to the studs may comprise looping the cord around each stud, and, before the studs are permanently anchored in position, driving the studs into the holes to grip the cord between the heads of the studs and the bone at the mouths of the holes, the free ends of the cords being sutured to the respective bones, or to tissue connected to said bones to maintain tension in the cord.

The method may include tensioning the cord by turning one of the studs about its axis by means of a tool engaging the head of the stud, prior to anchoring said stud permanently in position.

Instead, the connecting member may be a bone plate having a plurality of holes therethrough, the method comprising forming holes in each of two bone portions corresponding in position to the holes through the bone plate, placing the bone plate up against the bone portions so that the holes of the bone plate register with the holes in the bone portions, connecting the bone plate to the studs by inserting the studs through the holes in the bone plate and into the holes in the bone portions and then permanently anchoring the studs in position.

The invention, and its use, will now be described, by way of example, with reference to the accompanying diagrammatic drawings, in which:

FIG. 7 shows schematically, for a view of the stud according to FIG. 4, the positions and arrangement of the carbon fibres of the body;

FIG. 8 shows a view corresponding to FIG. 6, of a modified form of the stud of the kit according to the invention;

FIG. 9 shows a three dimensional view of a bone plate of a surgical implant kit according to the invention;

FIG. 10 shows a schematic diagram of the layout of the carbon fibres of the bone plate of FIG. 8;

FIG. 11 shows a longitudinal section of the bone plate of FIG. 8 in use;

FIG. 12 shows a side elevation of an anchor member forming part of a surgical implant kit according to the invention;

FIG. 13 shows a plan view of the anchor member of FIG. 12;

FIG. 14 shows schematically in part sectional side elevation a carbon tow forming part of a surgical implant kit according to the invention;

Figure 1:
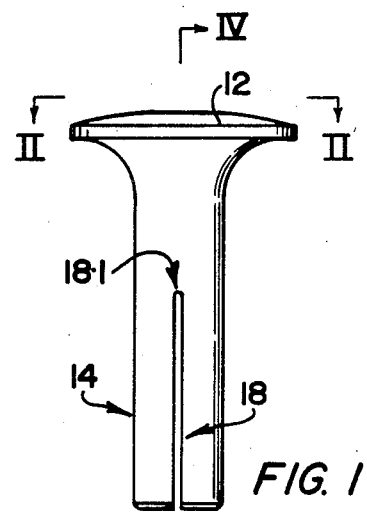
FIG. 1 shows a side elevation of the body of the stud of a surgical implant kit according to the invention.
Figure 2:
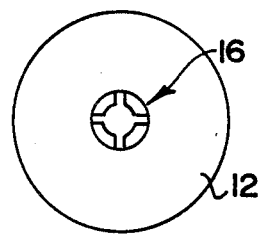
FIG. 2 shows an end elevation of the body of FIG. 1, along line II—II in FIG. 1.
Figure 3:
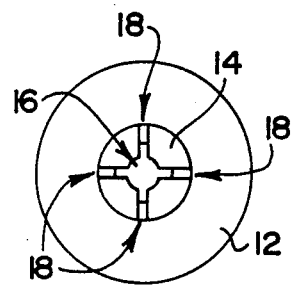
FIG. 3 shows the opposite end elevation of the body of FIG. 1.
Figure 4:
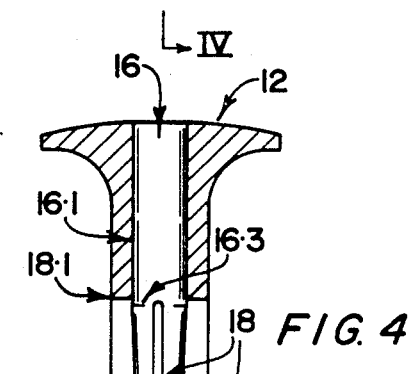
FIG. 4 shows a sectional side elevation of the body of FIG. 1 along line IV—IV in FIG. 1.
Figure 5:
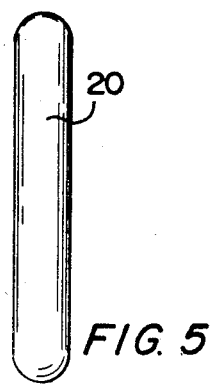
FIG. 5 shows a side elevation of the pin of the stud for use with the body of FIG. 1.

In FIGS. 1 to 7 of the drawings, a surgical implant in the form of a stud in accordance with the invention is generally designated 10. The stud 10 comprises a thermoplastic biocompatible matrix, e.g. biomedically acceptable polysulphone matrix, or a biodegradable cross-linked gelatine matrix, in which is embedded a plurality of carbon fibres. The stud has a head, generally designated 12, and an elongated cylindrical tubular body generally designated 14. The body and head have a central passage 16, extending along the full length of the stud, and the body has four circumferentially spaced elongated slits 18. The slits 18 extend axially along the body 14 from its end remote from the head 12, for somewhat more than half the length of the stud. The device further includes a cylindrical pin 20.

The passage 16 has a cylindrical portion 16.1 extending from the end of the stud provided with the head 12 to a position close to the closed ends 18.1 of the slits 18. The passage then has a tapering portion 16.2, which tapers from the inner end 16.3 of the straight portion 16.1, to the opposite end of the stud 10. The slits 18 are equally circumferentially spaced, so that the body 4 is cruciform in outline as viewed in FIG. 3, and the slits 18 extend inwardly from said opposite end of the stem, to positions 18.1 slightly closer to the head 12, than said inner end 16.3 of the portion 16.1. The pin 20 is slightly shorter than the passage 16, as can be seen from FIG. 6.

The pin 20 is of constant diameter and is circular in cross-section, and is of the same carbon fibre reinforced construction as the head 12 and body 14, having a plurality of carbon fibres extending substantially parallel to one another, along its length.

The head 12 and body 14 can be integrally formed from a suitable length of carbon fibre reinforced tubing. To do this the tubing has inserted into it a tapered pin, having the desired profile of the passage 16 (i.e. the cylindrical portion 16.1 and tapered portion 16.2) and the tubing is heated until the matrix softens. The tube is then moulded against the tapered pin to form the body 14 and passage 16, and the end of the tube through which the cylindrical portion 16.1 opens is subjected to axial compression, so that it bells outwardly to form the head 12. The matrix is then permitted to harden, after which the tapered pin is withdrawn from the head end. The slits 18 are then cut.

Instead, the body and head may be formed from a suitable length of carbon reinforced thermoplastic rod or bar, in which case the tapered pin forming the passage 16 is inserted axially into the rod or bar, after the rod or bar has been sufficiently softened by heating. The other forming operations are essentially the same.

The carbon fibres are shown diagrammatically at 22 in FIG. 7. From FIG. 7 it will be noted that the carbon fibres are substantially parallel to one another in the part of the body 14 around the portion 16.1 of the passage 16, and diverge slightly away from one another towards the end of the body remote from the head 12, around the tapering portion 16.2 of the passage 16. In the head 12, the fibres 22 curve outwardly and diverge from one another, as shown in the head 12 of FIG. 7, but are continuous and unbroken. However, it is contemplated that the body 14 and head 12 can instead be injection moulded with the fibres not necessarily continuous along the body 14 and parallel, but with the fibres possibly discontinuous but overlapping each other longitudinally and aligned more or less lengthwise along the body 14.

Figure 6:
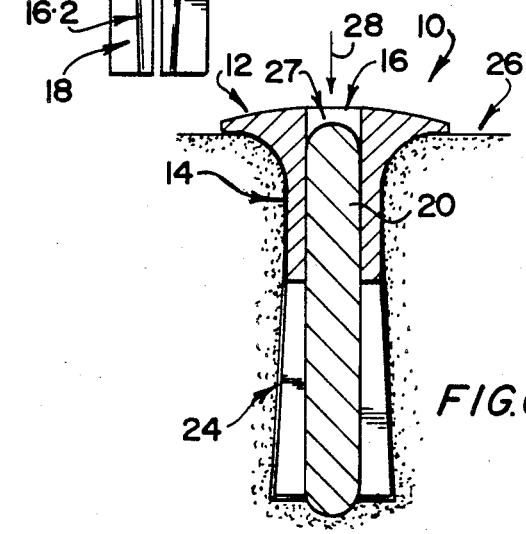
FIG. 6 shows a sectional side elevation, corresponding to FIG. 4, of the stud of the kit of the invention in position in a hole drilled in bone.

In use, with reference to FIG. 6, a hole 24 of a diameter slightly greater than that of the body 14 is drilled in bone 26 to which the stud 10 is to be anchored, and the body is then inserted, its end opposite the head 12 first, into the hole 24. The pin 20 is then hammered into the passage 16 from the head end, in the direction of arrow 28, for example by a suitable punch, until it is fully in position, as shown in FIG. 6. In this position, the pin 20, acts transversely (radially) to expand the part of the body 14 around the tapered portion 16.2 of the passage 16. This firmly and securely and more or less permanently locks the stud device 10 in position in the hole 24.

The pin 20 is hammered into the passage 16 until its inner end reaches the end of the passage remote from the head 12. Its outer end is then inwardly recessed from the end of the passage at the head, the recess 27 so formed acting as a drill guide for centering the tip of a drill, should it ever be necessary to drill the stud 10 out of the hole 24.

In FIG. 8 the same reference numerals are used as in FIGS. 1 to 7, unless otherwise specified, and a modified form of stud 10 is shown. The head 12 is shaped for engagement with a tool for turning the body 14 about its axis by having a screw driver slot 12.1.

The lower face of the head 12 has a peripheral rebate 12.2 and the head 12 is eccentric and offset transversely to one side with regard to the axis of the body 14. Thus, in FIG. 8, there is a greater thickness of material of the head (as at T) in a radial direction between the passage 16 and the rebate 12.2 on one side of the head than the other (as at t). The function of the rebate and eccentricity will be described hereunder with reference to FIGS. 12 to 17.

The stud 10 of FIGS. 1 to 7 can be used as part of an implant kit according to the invention with a connecting member in the form of a carbon fibre reinforced bone plate, for example of the type shown and described with reference to FIGS. 9 to 11 hereunder.

In FIGS. 9 to 11 the bone plate is generally designated 29. The bone plate 29 is shown in the form of an elongated flattened plate having parallel longitudinal side edges and a central series of spaced holes 31 extending along its length, at equally spaced positions.

The plate 29 is formed (FIG. 10) by winding and laying down a plurality of skeins or tows 30 of carbon fibres around a plurality of pins or pegs 32 in a mould. The tows 30 can be wound according to any suitable arrangement, whereby they are arranged to extend in directions, and to be located in positions, where they will best or at least efficiently serve to resist or combat anticipated stresses during use. A suitable arrangement is shown in FIG. 10. The tow starts to be laid out near the end of the plate at 30.1 and the finish thereof is at 30.2. Alternate tows can follow similar but different paths, the next tow starting and ending e.g. at corresponding positions near the other end of the plate 29. When sufficient, e.g. three, tows have been laid in position, the matrix can then be injected into the mould in molten form, or preferably introduced as a powder into the mould and melted in situ, and allowed to cool and harden to form the finished plate 29, the pegs 32 forming the openings 31 in the plate. However, the fibres or tows can if convenient be laid out at various more random angles in various alignments and can be of shorter staples, provided sufficient strength in the final product is obtained.

In use (FIG. 11) two bone portions 34, 36, separated by a diagonal break 38, may be connected together by means of the bone plate 29. Holes 24 (see also FIG. 6) are drilled in each of the fragments 34, 36, in positions corresponding to the openings 31 of the plate 29. Studs 10 are then anchored in position, through the openings 31 of the plate 29, to clamp the plate 29 to the fragments 34, 36, to hold them firmly and fixedly in position relative to each other. In this regard it will be appreciated that the size of the openings 31 corresponds with the diameter of the body 14 of the studs 10, the heads 12 of the studs engaging the peripheries, which are conveniently countersunk as shown at 31.1, of the holes 31 to hold the plate 29 in position.

In FIGS. 12 and 13 an anchor bar 39 forming part of a kit of the invention is shown. The bar 39 is broadly toggle shaped having two identical limbs 39.1 which extend away from each other from a corner 39.2 where they make an obtuse angle A with each other. The limbs 39.1 have their free ends 39.3 flattened to provide bearing surfaces 39.4 for bearing against bone as described hereunder. The radius of the anchor bar 39 excluding the flattened limb ends 39.4 is slightly more than 0.8 mm and it is made of a biocompatible material, which can be the same as that described above with reference to the studs 10, in which is embedded a plurality of carbon fibres at least some of which extend lengthwise and preferably for its full length, relative to the bar 39 from one end 39.4 to the other.

In FIG. 14 a cord in the form of a carbon fibre tow or skein is generally designated 40. The tow 40 comprises a bundle of a multiplicity of carbon fibres, of the type commonly used in carbon fibre technology, and each typically having a diameter of 0.008 mm, the tow 40 itself typically having a diameter of about 1½ mm. The fibres of the tow 40 are intertwined by being braided and/or twisted so that the tow is in the form of a rope which has a loop 40.1 at one end thereof. The individual fibres of the tow extend from the opposite end of the tow from the loop 40.1, along the length of the tow, around the loop 40.1 and back to said opposite end.

The tow 40 is impregnated with gelatine and the tow and gelatine are sterilized by irradiation after the impregnation. The gelatine contains a broad- or multi-spectrum bactericide, and acts to cause the fibres of the tow to adhere to one another while reducing the area of the tow exposed to the air by a factor of the order of 500 or more. The gelatine is selected to be free of pathogens or pathogenic organisms and fills the intestices between the fibres in the tow.

The tow 40 is provided with a connector 40.2 adhesively secured thereto e.g. by a suitable epoxy resin. The connector is in the form of a malleable metal wire having a loop 40.3 defining an eye 40.4 at each end of a shank portion 40.5. One of the loops 40.3 is embedded in said end of the two with the shank portion 40.5 and the other loop 40.3 projecting axially from the tow 40. The epoxy resin adhesively secures the fibres to the wire and also the fibres to themselves, particularly through the eye 40.4, to keep the embedded loop in position.

The portion of two containing the embedded loop 40.3 and adhesive, and the shank 40.5 outside the tow, are enclosed by a heat shrunk plastics sleeve 40.6 which shrinks more or less tightly onto said portion and shank. The part of the sleeve shrunk on the tow has a marginally greater diameter than the tow elsewhere and the sleeve tapers at 40.7 from the tow to said shank. The sleeve thus forms a forwardly tapering lead-in device for facilitating the pulling of the tow into passages in bone or other tissue while protecting the bones or tissue from the resin and protecting the forward end of the tow from mechanical damage as it passes along the passage.

In FIG. 15, again, the same reference numerals are used for the same parts, unless otherwise specified. A portion of bone 26 is shown with various surgical operations being carried out thereon in accordance with the method of the invention. At the top of FIG. 15 a bone drill 42 is shown having drilled a passage 44 through the bone 26. Below the bone drill 42 a bone cutter 46 is shown having countersunk and radiused the proximal end of a passage 44; and below that a further cutter 48 is shown having countersunk and radiused the distal end of a passage 44.

Below the cutter 48, the cutter 46 is shown drilling a hole 24 for a stud 10; and below that a stud 10 is shown partially inserted into a passage 24, with a tow looped bollard fashion around the body 14 below the head 12, the pin 20 being inserted only enough to hold it in place. Below that the stud is shown inserted fully into the hole, to clamp the tow against the bone 26 at the mouth of the hole 24, but with the pin 20 still only held frictionally in the outer end of the passage of the stud; while below that the pin 20 is shown driven fully into position to expand the part of the body 14 having the slits 18, permanently to anchor the stud in position.

Figure 15:
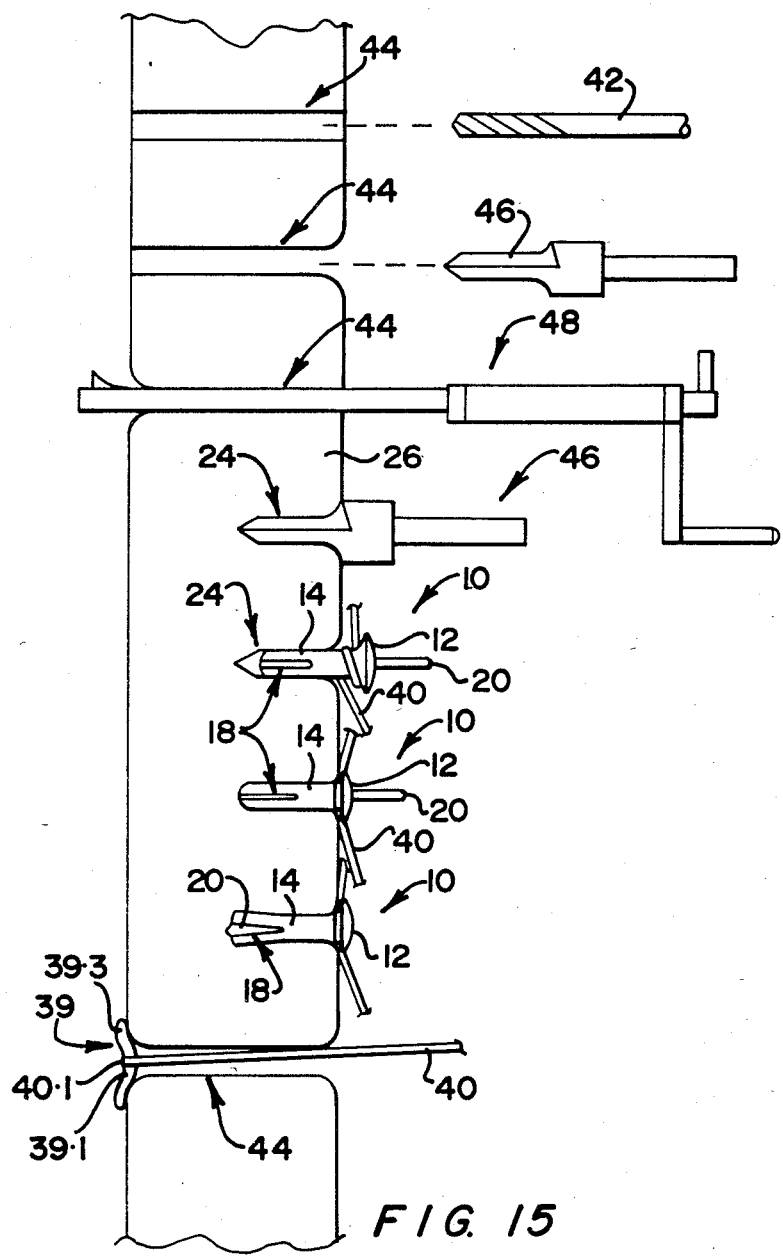
FIG. 15 shows schematically in sectional a portion of bone having various surgical techniques carried out thereon.

Lowermost in FIG. 15 is shown a passage 44 with a tow 40 extending therethrough, the loop 40.1 of the tow having an anchor bar 39 inserted therethrough. The loop 40.1 is located at the corner between the limbs 39.1 of the bar 39 and the tow 40 is under tension to pull the convex side of said corner into the mouth of the passage 44 with the flattened portions 39.3 of the bar 39 bearing against the bone 26 at the mouth of the passage 44.

Figure 16:
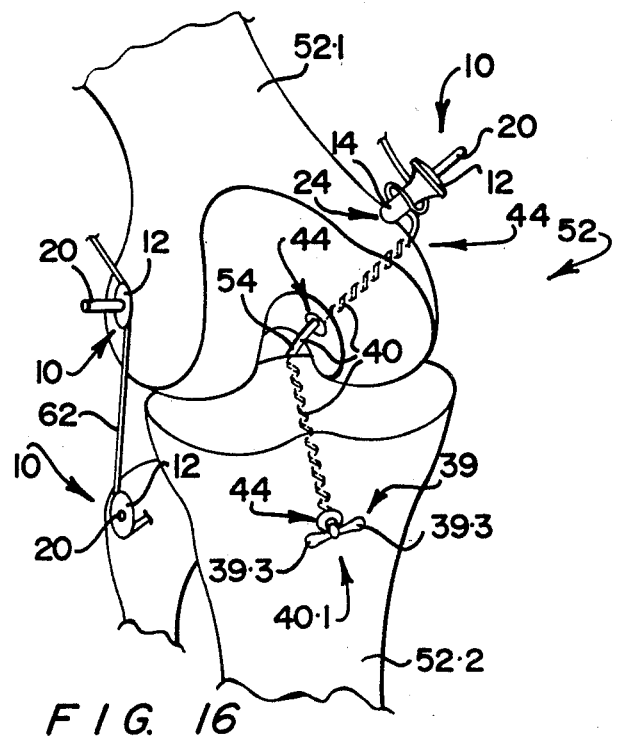
FIG. 16 shows a schematic view of a human knee joint during insertion of a kit according to the invention.
Figure 17:
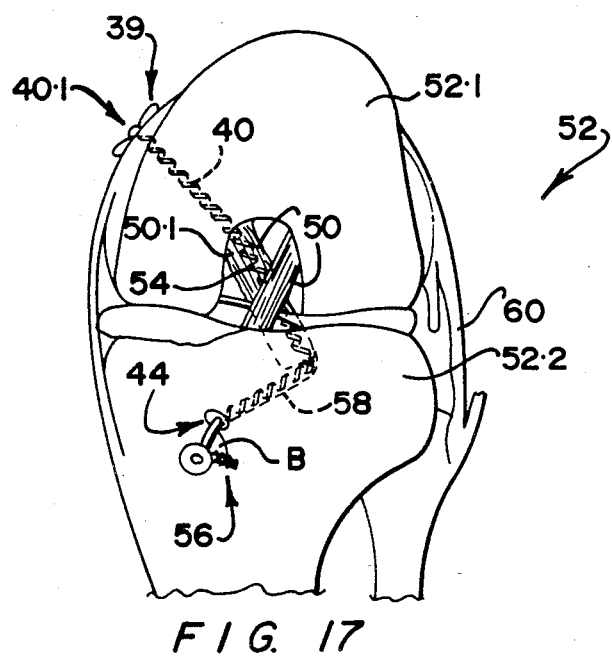
FIG. 17 shows a similar view of a knee joint after insertion of the kit.

With reference to FIGS. 16 and 17 (and again using the same reference numerals where appropriate), the studs 10 of FIGS. 1 to 7 are shown in use as an aid in joining together two bones whose interconnecting ligament has been ruptured. Such rupture can take place in the cruciate ligaments 50 in a human knee joint 52, between the femur 52.1 and tibia 52.2 as shown in FIGS. 16 and 17. In this case a sloping passage 44 is drilled through each bone, at a desired inclination and position, the passages 44 opening respectively out of the bone ends where the ruptured cruciate ligement would normally be attached, the opposite end of each passage opening out of the side of the bone in question, as close as convenient to the joint. The passage ends are countersunk and radiused and a tow 40 of carbon fibres is threaded through the passages 44, to extend along said passages 44 and at 54 in the position normally occupied by the cruciate ligament in question. The ends of the tow are then respectively anchored in position.

To thread the tow 40 into position a fish wire or the like is first threaded through the passages 44 (either separately or together, as convenient) and then an end of the fish wire is connected to the connector 40.3 of the tow (FIG. 14). The fish wire is then used to pull the tow 40 into position. When the tow 40 in in position, the anchor bar 39 is pushed through the loop 40.1 of the tow and is pulled via the tow up against the bone with the tow under tension. A hole 24 will have been drilled and countersunk near the proximal end of the passage 44 from which the tow emerges. The connector 40.2 (including the whole of the portion of the end of the tow containing the adhesive and the embedded loop 40.3 and covered by the sleeve 40.6) is cut off, the tow is looped around the body 14 of a stud 10 inserted partially into the hole 24. The tow is looped around the stud sufficient times (e.g. about 1½ turns as shown) to provide adequate frictional anchorage, bollard fashion, in use. The body 14 and head 12 are then driven home to clamp the tow against the bone (see FIG. 15), the pin 20 is then driven home to anchor the stud 10 permanently in position, and the free end of the tow is sutured to the bone or tissue connected to the bone, as shown at 56 in FIG. 17. This free end will be cut as short as possible while leaving sufficient length for easy suturing.

In FIG. 16 the tow 40 is threaded through the tibia 52.2 first and then through the femur 52.1 so that the stud 10 is in the femur 52.1 and the bar 39 acts on the tibia 52.2, while in FIG. 17 the arrangement is shown the other way round, the two having been threaded through the femur first so that the bar 39 acts on the femur and the stud 10 is in the tibia.

In FIG. 17 the ligament 50.1 has had its lower end detached from the top of the tibia 52.2. In this case a suture 58 is sutured to the detached end of the ligament 50.1, and the suture is threaded through the passage 44 in the tibia, wound around the stud 10 in the same fashion as the tow 40 and its free end is conveniently used to suture the free end of the tow 40 to the tibia 52.2. As the ligament can safely stretch by up to 5% of its length, the ligament 50.1 and suture 58 can be kept in tension with the ruptured end of the ligament at or in the distal end of the passage 44 in the tibia 52.2. Here it can grow back on to the tibia as essentially all the force of the knee joint is taken in use by the tow 40 and the ligament 50.1 is only moderately stressed. Preferably, the passage 44 in the femur is located so that its distal end opens out inside the roof of the ligament 50.1, the tow extending along the interior of the ligament 50.1 as shown.

The studs 10 of the invention can also be used to repair or replace the ligament 60 (FIG. 17) after rupture thereof. Thus in FIG. 16 a tow 62 is shown extending along the position of the ligament 60, its ends anchored to two studs 10 anchored in the same fashion as described above, in holes 24 drilled at appropriate positions for this purpose, the ends of the tow 62 being looped around the studs and sutured to the bone as described above. For this a tow 40 can be used, with the loop 40.1 and connector 40.2 removed to form the tow 62.

As far as the tow 40 and its use are concerned, it is contemplated that it will be pre-prepared, impregnated with gelatine, and with its connector and loop as described above. It will then be sterilized by irradiation and kept in sterile conditions in an airtight package, for example as part of a kit in the package, e.g. with a stud 10, anchor bar 39 and, optionally, suture material. It will be relatively stiff and robust in this condition and to use it the package will be opened shortly before the kit is implanted, the two being immersed in a sterile saline solution containing bactericide, for enough time for it to become soft, flexible and slippery and hence easy to pull through passages in bones and like tissue. In this condition, bearing in mind that it has the connector 40.2 with the malleable wire 40.3, 40.5 and the forwardly tapering sleeve 40.6 whose large end has a slightly greater diameter than the tow itself, it is easy and simple to pull through passages, even curved passages, in bone or the like, the tow being protected by the greater diameter of the sleeve from damage as it enters and passes through the passages, and the loop 40.1 being protected from damage in that it is never in use pulled through a passage.

With reference particularly to FIG. 8, final tensioning of the tow 40 can be effected before suturing its free end, by turning the head and body of the stud before the tow is clamped by the head of the stud and the pin 20 is driven in. The stud will be turned, e.g. by a screw driver, in the appropriate direction about its axis after the tow has been looped around the stud to increase the tension in the tow between the stud and anchor bar to the desired level, the body and head of the stud will be driven into the hole 24 to clamp the tow against the bone and the pin 20 will be driven in, after which the free end of the tow will be sutured. For driving the stud a two part punch can be used having a tubular outer portion for engaging and driving the head, within which is a central plunger for engaging and driving the pin 20. If desired, the head and body can also be turned after the body and head have been driven in but before the pin 20 is driven in.

In this regard the eccentric head of FIG. 8 is an advantage in that it permits the head to be turned by 180° from a position where the narrow portion of the head is on the opposite side of the head from the direction in which the tow extends away from the head towards the anchor bar (in which the tow is relatively slack), to a position where the thick part of the head is on said opposite side of the head, to tension the head before suturing. Furthermore, the eccentric head permits tensioning if desired, after suturing. In this case the tow is looped around the stud by more than 1½ turns so that the tow between the stud and the mouth of the passage 44 makes an angle, e.g. at B in FIG. 17, with the tow between the stud and the suture. Suturing is effected with the broad part of the stud head on the same side of the head as said angle B and with the tow relatively slack. The stud 10 can then be turned by 180° so that the broad part of the stud head is on the opposite side of the stud from said angle B, either before or after the stud head and body are driven into the hole to clamp the tow, thereby to tension the tow both between the stud and the suture and between the stud and the anchor bar, after which the pin 20 is driven in to anchor the stud permanently in position.

Although the use of the tow, stud and anchor bar have been described with reference to two passages in bone connected together by the tow, it will be appreciated that the passage in the bone in which the stud is anchored can in some cases be dispensed with, depending on the joint and damaged ligament in question. Thus the tow can extend from the anchor bar, through a passage in a bone, and then direct to the outside of the other bone, to which it is anchored by the stud, without passing through a passage in said other bone.

As mentioned above, the fibres of the tow will typically have a diameter of 0.008 mm and experience has shown that these fibres can snap if they are curved about a radius of less than 101.5 times their diameter. The diameter of the anchor bar and body of the stud, and the radius of the mouths of the passages, should thus be safely above 0.812 mm in practice for 0.008 mm fibres.

The method described with reference to FIG. 17 is of particular value with cases of acute tendon damage, where the ruptured tendon or its parts remain and can be sutured into position alongside or around the tow for subsequent regrowth into their original state. However, even in chronic cases (in practice about 1 in 15) where no ligament remains, the tow can be used to replace the ligament and there is a chance of a new ligament being regenerated along the path formed by the tow, to join the bones.

When no separate anchor bar 39 is used, it can be replaced e.g. by a tapered anchor member fast with the tow which replaces the loop 40.1 and is permanently fast with the tow. This feature is permitted by the provision of the connector 40.2 at the opposite end of the tow so that in use the anchor member need never pass through a passage.

An advantage of the invention is that it provides an inexpensive and yet easily used and easily sterilizable surgical stud implant, and implant kits including the stud. As the carbon, gelatine and matrix materials are biocompatible they need never be removed, and where the matrix materials are biodegradable, as with the gelatine, they can eventually be absorbed and excreted via the kidneys, permitting the implants to be invaded by bodily material. Thus new ligaments for example, can at least partially be regenerated and what material remains, such as the carbon fibres, is completely physiologically inert and can remain harmlessly in place for an indefinite period.

We claim:

1. A surgical implant comprising a stud and pin, said stud having an elongated tubular cylindrical body and an outwardly facing outer cylindrical surface, said body being smooth in both the longitudinal and the circumferential direction and having at one end thereof an enlarged head and an opposite end having means for enabling said body to undergo radially outward expansion; a longitudinal passage formed in said body connecting each of said ends wherein said passage is smooth and continuous; said pin being elongated and having a smooth outer surface such that the pin is slidable into said passage from said end having the head thereby to cooperate with said means for enabling said body to expand radially outwardly, to expand said body; said head being concavely radiused and said stud and said pin being of biocompatible materials, said body containing carbon fibres wherein said fibres are oriented longitudinally relative to the longitudinal axis of said stud.

2. A stud as claimed in claim 1, in which the body has at least one slit in its wall, extending away from its end remote from the head to facilitate expansion thereof by the pin.

3. A stud as claimed in claim 1, in which the pin is cylindrical, and in which at least part of the passage tapers in a direction towards its end remote from the head, whereby the body is transversely expandable by insertion of the pin from the direction of the head along the passage into said tapered part.

4. A stud as claimed in claim 1, in which the pin is shorter than the passage, so that it can be inserted into the body with its one end at the end of the passage remote from the head, and its other end inwardly recessed from the end of the passage at the head.

5. A stud as claimed in claim 1, in which the head is shaped for engagement with a tool for turning the body about its axis.

6. A stud as claimed in claim 5, in which the countersunk part of the head is eccentric, being offset to one side with regard to the body.

7. A stud as claimed in claim 1, in which the fibres at the head diverge and curve radially outwardly from one another into the head.

8. A surgical kit which comprises
a flexible cord for connecting together two bones in a mammal body, the cord comprising a tow of carbon fibres impregnated with a biocompatible material which causes the fibres to adhere to one another, the cord having a loop at one end thereof and the fibres extending from the end of the cord opposite the loop, along the length of the cord to the loop, around the loop and back to said opposite end, the cord being provided with a connector at said opposite end thereof for connection to pulling means for pulling the cord through a passage formed in bone, the connector comprising a length of flexible material having an eye at each end thereof, one of the eyes of the connector being embedded into the end of the cord and being adhesively secured thereto and the other eye being spaced from the end of the cord, the cord being adhesively secured to itself through said embedded eye and the part of the cord containing adhesive together with the connector between the end of the cord and the eye at the free end of the connector being covered by a sleeve in the form of a heat shrunk length of plastics tubing which tapers from where it surrounds the cord to where it surrounds the connector;
a surgical implant comprising a stud and pin assembly for anchoring said cord, said stud having an elongated tubular cylindrical body and an outwardly facing outer cylindrical surface, said body being smooth in both the longitudinal and the circumferential direction and having at one end thereof an enlarged head and an opposite end having means for enabling said body to undergo radially outward expansion; a longitudinal passage formed in said body connecting each of said ends wherein said passage is smooth and continuous; said pin being elongated and having a smooth outer surface such that said pin is slidable into said passage from said end having the head thereby to cooperate with said means for enabling said body to expand radially outwardly, to expand said body; said stud and said pin being of biocompatible materials, said body containing fibres wherein said fibres are oriented longitudinally relative to the longitudinal axis of said stud, and said fibres of the stud are carbon fibres.

9. A kit as claimed in claim 8 in which the biocompatible material which impregnates the tow comprises sterile gelatine.

10. A kit as claimed in claim 7, in which said fibers of said cord are twisted or braided.

11. A kit as claimed 8, in which the anchor member is in the form of a toggle shaped anchor bar having two limbs which extend away from each other from a corner where they make an obtuse angle with each other, the anchor bar having a radius which is at least 102 times that of the diameter of the carbon fibres of the tow, and the free ends of the limbs of the anchor bar being flattened to provide bearing surface for bearing against bone at the mouth of the passage through bone.

12. A kit as claimed in claim 8, in which the loop of the cord is permanently engaged with the anchor member.

13. A kit as claimed in claim 8, in which the flexible material of the connector comprises a length of malleable wire.

* * * * *

UNITED STATES PATENT AND TRADEMARK OFFICE
CERTIFICATE OF CORRECTION

PATENT NO. : 4,590,928
DATED : May 27, 1986
INVENTOR(S) : Michael S. HUNT et al

It is certified that error appears in the above-identified patent and that said Letters Patent is hereby corrected as shown below:

In claim 8, line 47 (last), after "fibers" insert -- ; and -- and as a separate paragraph -- an anchor member engageable with the loop for anchoring the cord at a position spaced from the stud, the anchor member being of at least one biocompatible material--.

Signed and Sealed this

First Day of November, 1988

Attest:

DONALD J. QUIGG

Attesting Officer

Commissioner of Patents and Trademarks